(12) United States Patent
Mtchedlidze

(10) Patent No.: US 8,318,219 B2
(45) Date of Patent: Nov. 27, 2012

(54) ISOLATED EXTRACT OF WALNUTS, METHOD FOR ITS OBTENTION AND ITS USE

(75) Inventor: Vakhtang Mtchedlidze, Barcelona (ES)

(73) Assignee: Hartington Business, S.L., Barcelona (ES)

( * ) Notice: Subject to any disclaimer, the term of this patent is extended or adjusted under 35 U.S.C. 154(b) by 0 days.

(21) Appl. No.: 13/483,639

(22) Filed: May 30, 2012

(65) Prior Publication Data

US 2012/0238637 A1 Sep. 20, 2012

Related U.S. Application Data

(63) Continuation of application No. 12/302,725, filed on Nov. 26, 2008, now Pat. No. 8,206,755.

(30) Foreign Application Priority Data

Jun. 2, 2006 (ES) .................................. 200601542

(51) Int. Cl.
*A61K 36/00* (2006.01)
*A61K 36/20* (2006.01)

(52) U.S. Cl. ......... 424/725; 424/771; 424/776; 424/777

(58) Field of Classification Search .................. None
See application file for complete search history.

(56) References Cited

FOREIGN PATENT DOCUMENTS

RU 2135200 C1 * 8/1999

* cited by examiner

*Primary Examiner* — Patricia Leith
*Assistant Examiner* — Randall Winston
(74) *Attorney, Agent, or Firm* — Barnes & Thornburg LLP

(57) ABSTRACT

The invention refers to an isolated extract of walnuts of high efficiency and stability over time useful for the manufacture of a medicament for the treatment of viral, fungal and bacterial diseases, which is characterized in that it is obtained from a process comprising: i) collecting unripe walnut fruits as raw material; ii) preparing the raw material for the extraction, iii) freezing the raw material prepared in the previous step; iv) drying; v) extracting in a time lower than 10 minutes; vi) filtration; and vii) final packaging. The invention also refers to its use for manufacturing a medicament for the treatment of bacterial, fungal and viral diseases and to a composition comprising it.

20 Claims, 2 Drawing Sheets

ISOLATED EXTRACT OF WALNUTS, METHOD FOR ITS OBTENTION AND ITS USE

CROSS REFERENCE TO RELATED APPLICATIONS

Figure 1:
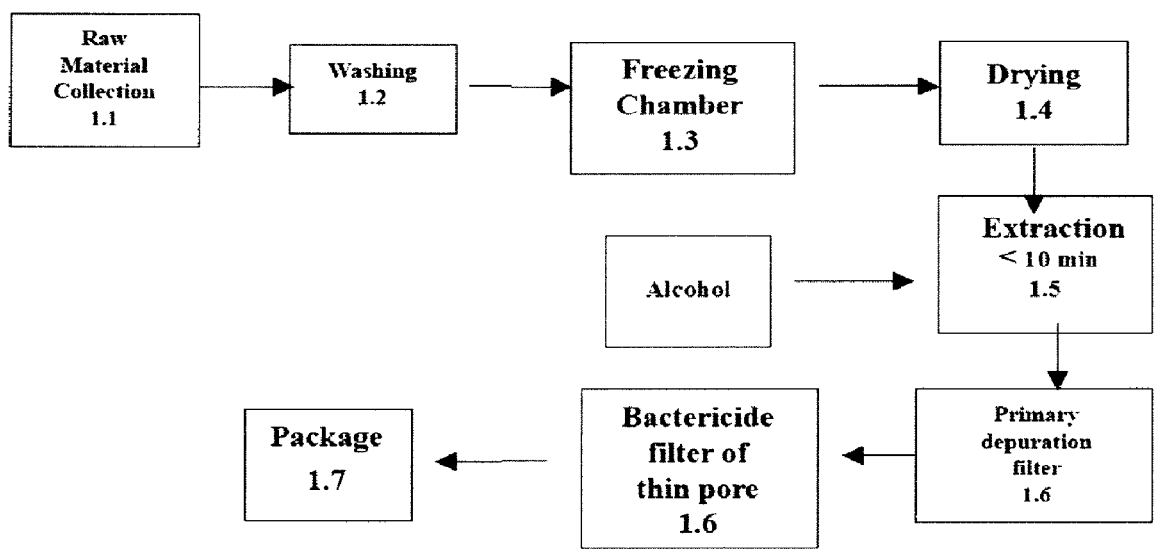

This application is a continuation application of U.S. application Ser. No. 12/302,725, filed on Nov. 26, 2008, which is a U.S. national application under 35 U.S.C. §371 of PCT Application Serial No. PCT/EP2007/055176 filed on May 29, 2007, which claims priority to Spanish Patent Application No. P-200601542, filed Jun. 2, 2006, the disclosures of which are hereby incorporated herein by reference.

FIELD OF THE INVENTION

The present invention refers to an isolated extract of walnuts with a high efficiency and stability over time useful for the manufacture of a medicament for the treatment of viral, fungal and bacterial diseases.

The present invention also refers to a process for obtaining said isolated extract of walnuts.

BACKGROUND OF THE INVENTION

The walnut extracts and cataplasms have been used during many years in popular dietetic medicaments.

The walnut tree contains at the bark, leafs or fruits gallic and catequic tannins, juglone, juglandine, carotene, inositol, pyrogallol, vitamin C and other substances.

It has been demonstrated that the walnut tree bark (Manchurian) contains mainly 5-hydroxi-1,4-naphtoquinones (juglone), 1,4,5-trihydroxinaphtalenes (hydrojuglone), glycosides of hydrojuglone, glycosides of hydroxi-$\alpha$-tetralone and gallic derivatives of these glycosides. It is also known that the walnut hull is very rich in vitamin C and that betacarotene, B1, B2 and B6 have been found in the leaves.

The juglone is considered as a natural product having antimicrobial, anti-neoplastic and anti-parasitic action and has anti-fungal and antiseptic properties. Therefore, it can be found in different market products, including colorant compositions for hair and oil of satin walnuts. The juglone, prepared from walnut hull, is an active ingredient active in dietetic complements.

There are evidences that suggest that the juglone is a strong chemotherapeutic or chemopreventive agent. The therapeutic development Program, National Cancer Institute (NCI) evaluated the juglone in its search for the HIV-1.

U.S. Pat. No. 6,296,838, from October 2001, refers to an anti-fungal composition, of topical application, for the treatment and prevention of the human nails infected with fungi. In particular, U.S. Pat. No. 6,296,838 describes that the extract with synergic effects contains a mixture of 10-15% of juglone extract from walnut hull with 20-30% of milled roots of *Nardostachys jatamansi* o *Vetiveria zizanioides* o *Catharanthus roseus*, because an extract of only juglone showed very little efficiency even in the long curing treatment and fungi-toxic effect.

To obtain said extract the walnut hulls were separated, washed with water and air dried. Then, they were milled and an extraction of juglone with solvents selected from acetone, alcohol and butanol was carried out. The solvent was removed from the extract and it was cooled to remove the waxes so that the juglone was partially fractionated.

The isolated extracts of walnuts described in the state of the art are based in the extraction of determined active ingredients with an anti-fungal, anti-microbial or anti-viral purpose, from a part of the tree whose active ingredient is found in great quantities.

There are anti-fungal compositions containing extract of juglone from walnut hull or compositions with a high concentration of vitamin C obtained from the tissues, walnut tree leaves, with a great content of vitamin C, among some of the most known.

The compositions comprising isolated extracts of walnuts present the drawback that it must be administered immediately after its preparation, said compositions having a short life because of the decrease of its effectiveness over time.

Therefore, because of the low stability of the isolated extracts of walnuts, the compositions containing them must be produced and administered within few days in order to provide a suitable effectiveness in the treatment.

Thus, said compositions based in isolated extracts of walnut have a limited application over time, because of the low stability of the juglone in the extract, and they are exclusively of anti-fungal, anti-microbial or anti-viral type.

Therefore, there has not provided yet any isolated extract from only walnuts which are stable over time and independent of the moment of preparation. Additionally, there has not been provided yet any composition containing said extract showing a simultaneous anti-fungal, anti-microbial and anti-viral application, whose properties are kept stable over time.

DESCRIPTION OF THE PRESENT INVENTION

A first aspect of the present invention is, therefore, to provide a walnut-based isolated extract stable over time and independent from the moment it was prepared.

A second aspect of the present invention is to provide a walnut-based isolated extract which is simultaneously effective in the treatment of fungi, bacteria and virus.

A third aspect of the invention is to provide a process permitting to obtain an isolated extract of walnuts according to the first and second aspects of the invention.

A fourth aspect of the present invention is the use of an extract according to the first aspect of the present invention for the manufacture of a medicament for the treatment of viral, fungal and bacterial diseases.

A fifth aspect of the invention is to provide a composition comprising an extract according to the first aspect of the invention to be used in the manufacture of a medicament for the treatment of viral, fungal and bacterial diseases.

DEFINITIONS

In the present invention by "unripe fruits of walnuts" is meant that said walnuts are in a Lactic-Waxy ripeness state. In general, said ripeness state takes places between 10th of June and 15th of September, more approximately from 10th of July and 10th of August, even though said dates can vary a little according to the weather of the place where the fruit is ripening.

FIGURES

FIG. 1 shows a flow chart of the process according to the present invention where the obtention of a walnut extract with an extraction time lower than 10 min. is carried out.

Figure 2:
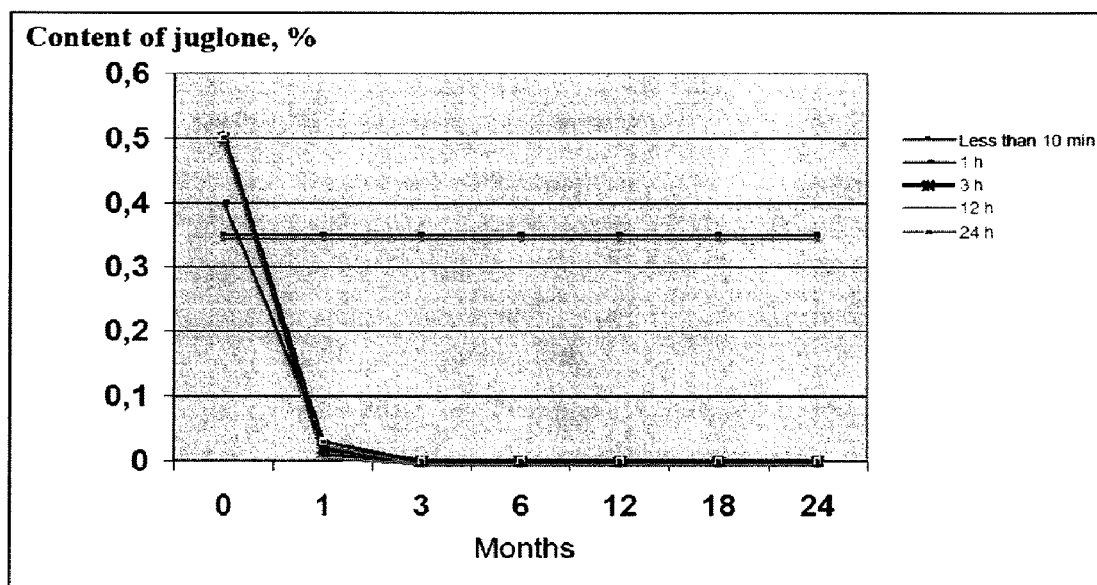

FIG. 2 refers to a graphical representation of the content of juglone in (%) in a walnut extract in respect with the time from its preparation, as a function of the time used during the extraction step. From said FIG. 2 it can be seen that the content of juglone was kept stable over time only when the extraction time is lower than 10 min. (—■—).

DETAILED DESCRIPTION OF THE INVENTION

The inventors of the present invention have found that the extraction time used during a walnut extract is obtained is a decisive condition in the final properties of the obtained extract.

Advantageously, the isolated extract of walnuts according to the first aspect of the invention shows properties for a simultaneous anti-fungal, anti-microbial and anti-viral application which is stable over time.

According to the three first aspects of the invention, there is provided an isolated extract of walnuts which characterized in that it is obtained from a process comprising:
 i) Collecting unripe walnut fruits as raw material;
 ii) Preparing the raw material for the extraction;
 iii) Freezing the raw material prepared in the previous step;
 iv) Drying;
 v) Extracting in a time lower than 10 minutes;
 vi) Filtration; and
 vii) Final packaging.

In particular, the preparation of the raw material for the extraction (ii) comprises preferably a mechanical cleaning, a washing with running water, a washing with distilled water and a drying at the air.

Preferably, the freezing step (iii) comprises keeping the walnut fruits in a frozen chamber at a temperature comprised between −18 and −20° C. during 70-170 hours, even more preferably during about 120±5 hours.

In particular, the drying step (iv) comprises, first, peeling the shells of the frozen walnut in thin layers of 2 to 3 mm and, then, place them in trays to leave them dry, preferably under the sun and then in a drying chamber at a temperature of 38° C.±2° C. until a humidity lower than 10% is obtained.

The extraction step (v) comprises breaking the obtained dried mass, in the drying step, into little pieces, and adding ethyl alcohol (96%) in a 1/2 to 1/5 weight/volume ratio, preferably 1/3, and carrying out an extraction during a time lower than 10 minutes, preferably lower than 5 minutes, even more preferably lower than 2 minutes.

The filtration step of the extract is carried out preferably in a primary depuration filter and, then, in a bactericide filter of thin pore at a pressure of 0.25±0.005 MPa.

There are also included within the scope of the present invention those modifications that a person skilled in the art can carry out in the steps i) to iv), vi) and vii), providing that they do not depart from the inventive concept object of the present invention. As a non-limiting diagram of the invention of the process defined above see FIG. 1.

The inventors of the present invention have found that the extraction time is critical in the final properties of the isolated extract of walnuts. It is believed that when the extraction time is increased, other components are removed from the walnut that possibly interfere in the stability and efficiency over time of the obtained extract.

Surprisingly, the inventors of the present invention have found that the isolated extract of walnuts obtained according to the first aspect of the invention retains its properties for a simultaneous anti-fungal, anti-microbial and anti-viral application, apart from being stable over time.

Therefore, the invention also provides a process for obtaining an isolated extract of walnuts as defined above according to the first aspect of the invention.

The inventors of the present invention evaluated the stability of the juglone as a function of the time used during the extraction step v).

In Table 1 below it can be seen that the longer extraction time is used in step v), the lower is the stability over time of the active ingredient juglone.

TABLE 1

| Assay No. | Extraction Time (h) | Months | | | | | | | |
|---|---|---|---|---|---|---|---|---|---|
| | | 0 | 15 days | 1 | 3 | 6 | 12 | 18 | 24 |
| 1 | <10 min | 0.35 | 0.35 | 0.35 | 0.35 | 0.35 | 0.35 | 0.35 | 0.35 |
| 2 | 1 | 0.4 | 0.08 | 0.03 | 0 | 0 | 0 | 0 | 0 |
| 3 | 3 | 0.5 | 0.06 | 0.02 | 0 | 0 | 0 | 0 | 0 |
| 4 | 12 | 0.5 | 0.05 | 0.01 | 0 | 0 | 0 | 0 | 0 |
| 5 | 24 | 0.5 | 0.09 | 0.03 | 0 | 0 | 0 | 0 | 0 |

From the results shown in Table 1, it can be seen that the content of juglone in the final extract decreased when the extraction time of step v) is increased, and also decreased the stability of the juglone extract over time after its preparation.

Surprisingly, the juglone extract obtained using an extraction time lower than 10 min was kept stable after its preparation during a time up to 24 months and, therefore, its efficiency did not depend on the time from its preparation, but the time used during the extraction time, see assay No. 1 and FIG. 2.

Advantageously, with the isolated extract of juglone according to the first aspect of the present invention an extract is obtained with a stability of more than two years, stability substantially longer compared to the walnut extracts disclosed in the state of the art of approximately some days.

The isolated extract of walnuts according to the present invention has application in the treatment of herpes, chickenpox, fungi on the skin, nails, etc., in general in the treatment of skin diseases.

The administration of the extract according to the present invention can be carried out by topical, intraperitoneal or oral application such as, e.g. liquid form, creams or tablets, even though other ways of application of the extract according to the present invention are also included in the scope thereof.

The inventors of the present invention also studied the efficiency of the isolated extract according to the first aspect of the invention in bacteria, fungi and virus of the assays No. 1 to 5 (Table 1). See Table 2 below.

TABLE 2

| Months | Type | Extraction time | | | | |
|---|---|---|---|---|---|---|
| | | <10 min (No. 1) | 1 h (No. 2) | 3 h (No. 3) | 12 h (No. 4) | 24 h (No. 5) |
| 0 | Staphylococus ATCC 6538 | (+) | (+) | (+) | (+) | (+) |
| | Pseudomonas aeruginosa ATCC 9027 | (+) | (+) | (+) | (+) | (+) |
| | Aspergillus niger ATCC 16404 | (+) | (+) | (+) | (+) | (+) |
| | Candida albicans ATCC 10231 | (+) | (+) | (+) | (+) | (+) |
| | Herpes simplex virus type 1 HSV-1 | (+*) | (+*) | (+*) | (+*) | (+*) |
| 6 | Staphylococus ATCC 6538 | (+) | (−) | (−) | (−) | (−) |
| | Pseudomonas aeruginosa ATCC 9027 | (+) | (−) | (−) | (−) | (−) |
| | Aspergillus niger ATCC 16404 | (+) | (−) | (−) | (−) | (−) |
| | Candida albicans ATCC 10231 | (+) | (+) | (+) | (+) | (+) |
| | Herpes simplex virus type 1 HSV-1 | (+*) | (−*) | (−*) | (−*) | (−*) |
| 12 | Staphylococus ATCC 6538 | (+) | (−) | (−) | (−) | (−) |
| | Pseudomonas aeruginosa ATCC 9027 | (+) | (−) | (−) | (−) | (−) |
| | Aspergillus niger ATCC 16404 | (+) | (−) | (−) | (−) | (−) |
| | Candida albicans ATCC 10231 | (+) | (+) | (+) | (+) | (+) |
| | Herpes simplex virus type 1 HSV-1 | (+*) | (−*) | (−*) | (−*) | (−*) |
| 24 | Staphylococus ATCC 6538 | (+) | (−) | (−) | (−) | (−) |
| | Pseudomonas aeruginosa ATCC 9027 | (+) | (−) | (−) | (−) | (−) |
| | Aspergillus niger ATCC 16404 | (+) | (−) | (−) | (−) | (−) |
| | Candida albicans ATCC 10231 | (+) | (+) | (+) | (+) | (+) |
| | Herpes simplex virus type 1 HSV-1 | (+*) | (−*) | (−*) | (−*) | (−*) |

Table Foot:
(+) Depresses Growth;
(−) Not Depresses Growth;
(+*) Depresses Reproduction of HSV-1 virus in DR cell cultures (bone sarcoma) and of human musculocutaneos fibroblasts;
(−*) Not Depresses Reproduction of HSV-1 virus in DR cell cultures (bone sarcoma) and of human musculocutaneos fibroblasts;

From the data shown in the previous table it can be seen that when the extraction time was increased, the extract lost efficiency over time from the moment of its production.

The shown results prove that the isolated extract of walnuts according to the first aspect of the invention retains its efficiency over time in bacteria, fungi and virus up to 24 months from its preparation and that said efficiency depends on the time used during the extraction step (assay No. 1).

Therefore, according to the fourth aspect of the present invention there is also provided an isolated extract of walnuts which is used for the manufacture of a medicament for the treatment of viral, fungal and bacterial diseases.

The invention also refers to a composition comprising an extract according to the first aspect of the invention and to its use for the manufacture of a medicament for the treatment of viral, fungal and bacterial diseases.

Hereinafter some cytoxicity studies proving that the extract according to the first aspect of the present invention is suitable to be used in humans are included.

General Toxicity Studies

The toxicological evaluation of the isolated extract of walnuts according to the first aspect (hereinafter, the extract) was carried out in rats and mice to which different concentrations of the extract were intragastrically administered. The intragastrical administration was proposed in order to obtain a systemic effect on the herpes virus, both in cases of acute infection and in virus carriers. The extract can be considered, hence, a natural antiviral chemotherapeutical remedy. However, the manifestation of its toxic properties was expected because it was administered by systemic absorption, which was also confirmed in a sub-acute study with rats and mice. It must be pointed out, however, that the frequency of fatal ends, even when maximum doses are administered intragastrically, is so low that it is impossible to establish average lethal doses ($LD_{50}$, etc.). The extract has neither the property of material accumulation nor a mutagenic effect on bone marrow cells.

About the general toxic properties, it is necessary to point out the effect on CNS and the inhibitory action on the growing of the body mass in baby animals. The toxicity related to the parenchymatous organs consists of, in particular, the deterioration of the parenchymatous cells of the liver and to the alteration of the excretory function of kidneys. The reduction of the spleen and adrenals mass seems to reflect the stress state as a result of the long-term manipulations for 30 days (see table 1.1, ethanol 5%).

Likewise, the extract doses which cause minimum deviations of the normal indexes in rats have been established, and this has been taken conventionally as the maximum tolerable dose administering 0.5 ml of 0.5% solution for 30 days. In humans, this is equivalent to 250-500 ml of solution at said concentration. Actually, as it is well-known, in clinical conditions $1/100$-$1/10$ of the minimum toxic dose or "inactive" dose are assayed, which represents 2.5-5.0 ml of 0.5% solution per day.

In conclusion, the results of the toxicological evaluation of the solutions of Ext at different concentrations applied cutaneously several times show that the preparation at a dose of 0.2 ml of 5% solution does not cause evident intoxication effects. However, histologically, certain grade of intensification of the keratinization process in the epidermis is shown without any increase of the layers of the epidermic cells and without inflammatory effects on the skin itself (the dermis).

The 50% extract solution produces evident hyperkeratosis, dryness and hardening of the cutaneous folds. Histologically, together with the intensification of the keratinisation process, an increase of the cell layers in the epidermis is also produced, even though in this case no inflammatory effects have been observed. With this dose no systemic toxicity (by absorption) signs have been observed.

In two weeks long experiment with mice, the animals received volumes of about 4 times greater than the solutions at the same concentrations (5 and 50% solutions). The visual cutaneous reaction in a shedding and thickening manner of the cutaneous folds, histologically confirmed, without inflammatory effects, is already shown when using 5% Ext. A granulocytopoietic reaction is also seen, shown in the transformation of the "lymphocytary" type, of hemopoiesis, characteristic of the rodents, to "granulocytary" type. The preparation at a concentration of 5% did not produce any destructive or inflammatory change in the mucous membrane of the distal segment of the rectum. At this dose no symptom of a general systemic toxic effect was observed. The application on the skin of extract at a extremely high concentration (50%) is accompanied by systemic toxicity effects. The characteristic properties of the preparation are also observed, specifically, the stimulation of the keratinisation and the granulocytopoiesis (granulocytosis) with no inflammatory effects on the skin and the mucous membrane.

When intense transdermal absorption of the preparation is simulated, using a subcutaneous route of administration, the most characteristic sign of the systemic effect is the neurotoxicity with prevalence of CNS depression phenomena.

Taking as a base the determination of the average toxic doses and others in mice ($TD_{50}$—0.4 ml of solution at 17±3.8%, $TD_{16}$—0.4 ml of solution at 10%, $TD_{84}$—0.4 ml of solution at 35% in animals), as an approximate non-toxic dose in conditions of local cutaneous application in rats the dose of 1.0-1.5 ml/Kg of 5% solution is taken.

The extract solutions at a concentration of 5-50° have neither local irritant nor sensitizing (allergenic) properties when are cutaneously applied.

Studies of Anti-Viral Activity

The objective of the present study was to examine the isolated extract of walnuts according to the first aspect used in the manufacture of a preparation (hereinafter, the extract) in order to prove the presence of anti-viral activity (anti-herpes) in cell cultures. As an experimental model the following cells were used: continue cell line DR of bone sarcoma (obtained from the virology laboratory of the National Centre of Georgia of especially dangerous infections) and primary culture of human fibroblasts of musculocutaneous origin (abortive material, from the Institute of obstetrics, gynaecology and perinatal medicine of the Ministry of Health of Georgia). Viral material—herpes simplex virus type I, obtained from the museum of the virology laboratory of the Institute of viral preparations of the Ministry of Health of the Russian Federation (Moscow).

In order to carry out the experiment the method of cross valuation was used, which includes the simultaneous analysis of different concentrations of the extract (from 1:5 to 1:80) and of different dilutions of the virus (from 1:10 to 1:10,000,000; traditionally, it is designated in the following way: from −1.0 lg to −7.0 lg). This method permits to show the more little nuances of the interaction between said preparations and the doses, as well as to show an optimal variant of maximum protection of the cells against the viral infection (Zdrodovski P. F., Sokolov M. I.—Rukovodstvo po laboratornoy diagnostike virusnikh i rikketsioznikh bolezney [Manual of analytical diagnostic of viral and rickettsian diseases//M., "Meditsina", 1965, c396).

The analysis of the obtained results permitted to univocally conclude that the vegetal extract used for the manufacture of the preparation was able to produce the inhibition of the reproduction of the herpes simplex virus in DR cell cultures (bone sarcoma) and musculocutaneous human fibroblasts. This effect was more intense when the extract was used in a dilution of 1:5 (the pure extract was not assayed intentionally taking into account the possibility of a citotoxic effect on the cells). The method of cross valuation of the extract and the virus in cell cultures permitted to demonstrate the protective anti-herpes effect of the extract and to find out some regularities of the course of the infection in the cells.

Studies of Anti-Herpes Activity

In in-vitro studies, the isolated extract of walnuts according to the first aspect (hereinafter, the extract) demonstrated to have protective properties against to herpes simplex virus (HSV) in cell cultures of human fibroblasts and DR bone sarcoma, so that it was considered necessary to study the anti-viral effect of the extract in white mice.

To do this, an herpes infection model in white mice was used to study the mortality of the animals and the reproduction index of the virus. The state of the immune system of the organism was evaluated in terms of antibody production, phagocytosis and interferon activity. The embriotoxic and mutagenic effect of the herpes virus and the state of the antioxidant protection in pregnant females of mouse were also analysed. All these parameters were studied in infected mice treated with the extract.

In conclusion, the studies demonstrated convincingly that the extract could be used successfully to neutralize selectively the immunodepressant effect of the herpes virus. We can argue the different mechanisms of the properties of the extract we have indicated, but the most acceptable are the following: in presence of herpes virus, an hormonal unbalance is generated in the organism, a general and cell hypoxia is developed and the destructive processes lead to an intoxication. All these phenomena are either originated from an existing immunopathology or caused from themselves. In other words, in the presence of herpes virus, at least all said four factors are produced: hormonal unbalance, hypoxia, intoxication and immunopathology, with mutually aggravating effects.

One of the mechanisms of the protection effect of the extract is its antioxidant properties, which favour the re-establishment of the breath at intracellular level (including the immunocytes). It is believed that the extract produces these effects by means of the active physiological substances contained in it (antibiotic, Juglone and flavonoids; micro-elements; complex of vitamins C, E, PP), which favour the intensification of the functional activity of the immunocompetent cells.

Therefore, the extract can be classified without any doubt among the active natural remedies that can be used efficiently in the prevention and the treatment of viral and bacterial infections, the pyogenic and inflammatory diseases, as well as other pathological states which require an enhancement of the metabolic and adaptive processes.

The invention claimed is:

1. An isolated, stable juglone extract of walnuts, the juglone extract obtained by a process comprising the steps of:
   i) obtaining unripe walnut fruits as raw material;
   ii) preparing the raw material of step i) for extraction;
   iii) freezing the prepared material of step ii);
   iv) drying the frozen material of step iii);
   v) extracting the dried material of step iv) by adding an alcohol to the dried material at a ratio from about 1:2 to about 1:5 (weight/volume); and
   vi) filtering the extracted material of step v);
   wherein step v) is performed in a time of about 10 minutes or less; and
   wherein the extract is stable for a period up to 24 months.

2. The juglone extract of claim 1, wherein the extract exhibits anti-viral, anti-bacterial, and anti-fungal properties.

3. The juglone extract of claim 1, wherein the extract has anti-oxidant properties.

4. The juglone extract of claim 1, wherein the preparation of the raw material for step (ii) comprises
   A) cleaning the raw material via mechanical means,
   B) washing the raw material, and
   C) drying the raw material.

5. The juglone extract of claim 1, wherein step (iii) comprises freezing the prepared material of step ii) at a temperature of about −18° C. to about −20° C. for a time period of about 70 hours to about 170 hours.

6. The juglone extract of claim 1, wherein step (iv) comprises
A) peeling the shells of the frozen material of step iii) in thin layers of about 2 mm to about 3 mm, and
B) drying the frozen material of step iii) to a humidity lower than about 10%.

7. The juglone extract of claim 1, wherein the alcohol is ethylic alcohol (96%).

8. The juglone extract of claim 1, wherein the alcohol is added at a ratio of about 1:3 (weight/volume).

9. The juglone extract of claim 1, wherein step v) is performed in a time of about 5 minutes or less.

10. The juglone extract of claim 1, wherein step v) is performed in a time of about 2 minutes or less.

11. The juglone extract of claim 1, wherein step vi) is first performed in a primary depuration filter and subsequently performed in a thin pore bactericide filter.

12. A method of treating a disease in a patient, said method comprising the step of administering to the patient a therapeutically effective dose of the extract of claim 1, wherein the disease is selected from the group consisting of a viral disease, a bacterial disease, and a fungal disease.

13. A method of treating a viral infection in a patient, said method comprising the step of administering to the patient a therapeutically effective dose of the extract of claim 1.

14. The method of claim 13, wherein the viral infection is caused by herpes simplex virus (HSV).

15. The method of claim 13, wherein the viral infection is a skin infection.

16. The method of claim 13, wherein the extract neutralizes the immunodepressant effect of the viral infection.

17. The method of claim 13, wherein the extract is administered as an application selected from the group consisting of a topical application, an intraperitoneal application, or an oral application.

18. The method of claim 13, wherein the extract is administered as a solution.

19. The method of claim 18, wherein the solution contains the extract at a concentration between about 5% and about 50%.

20. The method of claim 13, wherein the extract is administered topically as a solution.

\* \* \* \* \*

UNITED STATES PATENT AND TRADEMARK OFFICE
CERTIFICATE OF CORRECTION

| | | |
|---|---|---|
| PATENT NO. | : 8,318,219 B2 | Page 1 of 1 |
| APPLICATION NO. | : 13/483639 | |
| DATED | : November 27, 2012 | |
| INVENTOR(S) | : Vakhtang Mtchedlidze | |

It is certified that error appears in the above-identified patent and that said Letters Patent is hereby corrected as shown below:

On the first page of the Patent at item (63), please correct the priority claim information to read as follows:

-- Continuation of application No. 12/302,725, filed as application No. PCT/EP2007/055176 on May 29, 2007, now Pat. No. 8,206,755. --

Signed and Sealed this
Twelfth Day of February, 2013

Teresa Stanek Rea
*Acting Director of the United States Patent and Trademark Office*